United States Patent
Hernandez Altamirano et al.

(10) Patent No.: US 9,920,019 B2
(45) Date of Patent: Mar. 20, 2018

(54) MULTIFUNCTIONAL COMPOSITION BASE 1,3-OXAZINAN-6-ONES WITH CORROSION INHIBITION AND HEAVY ORGANIC COMPOUNDS INHIBITION AND DISPERSANTS AND OBTAINING PROCESS

(71) Applicant: INSTITUTO MEXICANO DEL PETROLEO, Mexico City (MX)

(72) Inventors: Raul Hernandez Altamirano, Mexico City (MX); Violeta Yasmin Mena Cervantes, Mexico City (MX); Luis Silvestre Zamudio Rivera, Mexico City (MX); Hiram Isaac Beltran Conde, Mexico City (MX); Eduardo Buenrostro Gonzalez, Mexico City (MX)

(73) Assignee: Instituto Mexicano del Petroleo, Mexico City (MX)

( * ) Notice: Subject to any disclaimer, the term of this patent is extended or adjusted under 35 U.S.C. 154(b) by 16 days.

(21) Appl. No.: 14/581,761

(22) Filed: Dec. 23, 2014

(65) Prior Publication Data

US 2015/0112060 A1   Apr. 23, 2015

Related U.S. Application Data

(62) Division of application No. 13/097,236, filed on Apr. 29, 2011, now Pat. No. 9,108,935.

(30) Foreign Application Priority Data

Apr. 30, 2010 (MX) .................... MX/a/2010/004777

(51) Int. Cl.
*C09K 8/54* (2006.01)
*C07D 265/10* (2006.01)
(Continued)

(52) U.S. Cl.
CPC .......... *C07D 265/10* (2013.01); *C07C 227/10* (2013.01); *C09K 8/524* (2013.01); *C09K 8/54* (2013.01); *C10G 75/02* (2013.01); *C10L 1/14* (2013.01); *C10L 1/233* (2013.01); *C10L 10/00* (2013.01); *C10L 10/04* (2013.01); *C10G 2300/1033* (2013.01); *C10G 2300/206* (2013.01); *C10G 2300/4075* (2013.01); *C10G 2300/44* (2013.01); *C10G 2300/80* (2013.01); *C10G 2400/02* (2013.01); *C10G 2400/04* (2013.01); *C10G 2400/08* (2013.01); *C10L 1/1608* (2013.01); *C10L 1/1616* (2013.01); *C10L 1/1824* (2013.01); *C10L 2200/0259* (2013.01); *C10L 2200/043* (2013.01); *C10L 2200/0423* (2013.01); *C10L 2200/0446* (2013.01); *C10L 2230/08* (2013.01);
(Continued)

(58) Field of Classification Search
CPC . C09K 8/68; C09K 8/52; C09K 8/584; C09K 8/12; C09K 8/36; C09K 8/64; C09K 8/685; C09K 8/80; C09K 8/885; C09K 8/905; C09K 21/08; C09K 2208/08; C09K 2208/10; C09K 2208/22; C09K 2208/28; C09K 2208/32; C09K 2208/34; C09K 3/30; C09K 5/10; C09K 8/035; C09K 8/08; C09K 8/32; C09K 8/426; C09K 8/44; C09K 8/46; C09K 8/487; C09K 8/502; C09K 8/5083; C09K 8/5086; C09K 8/512; C09K 8/516; C09K 8/528; C09K 8/58; C09K 8/588; C09K 8/594; C09K 8/70; C09K 8/82; C09K 8/882; C09K 8/887; C09K 8/90; C09K 8/92; C09K 8/94; C09K 8/54
See application file for complete search history.

(56) References Cited

U.S. PATENT DOCUMENTS 3,390,085 A   6/1968  Floeck
3,623,979 A   11/1971 Maddox et al.
(Continued)

FOREIGN PATENT DOCUMENTS

JP   2001181245   * 7/2001
WO  WO2008/130214  * 11/2008

OTHER PUBLICATIONS https://en.wikipedia.org/w/index.php?title=Dean-Stark_apparatus&printable=yes, downloaded on Apr. 27, 2016.*
(Continued)

*Primary Examiner* — Kumar R Bhushan
(74) *Attorney, Agent, or Firm* — Dickinson Wright, PLLC

(57) ABSTRACT

Base compounds including 1,3-oxazinan-6-one derivatives of N-alkyl or N-alkenyl or N-cycloalkyl or N-aryl propionic acids and paraformaldehyde, and their application as corrosion inhibitors with multifunctional properties serving as inhibitory/dispersant of asphaltene in production processes, transportation, refining and storage of crude oil and derivatives. The corrosion inhibitor with inhibitory/dispersant of asphaltenes properties comprises an active substance base of 1,3-oxaninan-6-ones and hydrocarbon solvents such as benzene, toluene, mixed xylenes, o-xylene, m-xylene and p-xylene, diesel, kerosene, jet fuel, alcohols, aliphatic branched and unbranched alcohols containing from 3 to 10 carbon atoms, such as isopropanol, butanol and pentanol, and mixtures of hydrocarbon solvents with aliphatic branched or unbranched liquid fuels. In addition, a process for obtaining 1,3-oxazinan-6-ones derivatives of N-alkyl or N-alkenyl or N-cycloalkyl or N-aryl propionic acids and paraformaldehyde is described.

11 Claims, 1 Drawing Sheet

(51) Int. Cl.
C09K 8/524 (2006.01)
C10L 1/14 (2006.01)
C10L 1/233 (2006.01)
C10L 10/00 (2006.01)
C10L 10/04 (2006.01)
C10G 75/02 (2006.01)
C07C 227/10 (2006.01)
C10L 1/16 (2006.01)
C10L 1/182 (2006.01)

(52) U.S. Cl.
CPC ..... *C10L 2230/14* (2013.01); *C10L 2270/023* (2013.01); *C10L 2270/04* (2013.01); *C10L 2270/10* (2013.01)

(56) References Cited

U.S. PATENT DOCUMENTS

| | | | |
|---|---|---|---|
| 3,629,104 A | 12/1971 | Maddox | |
| 4,214,876 A | 7/1980 | Garth et al. | |
| 4,388,214 A | 6/1983 | Oppenlaender et al. | |
| 4,509,951 A | 4/1985 | Knapp | |
| 4,511,366 A | 4/1985 | Burrows et al. | |
| 4,737,159 A | 4/1988 | Phillips | |
| 5,062,992 A | 11/1991 | McCullough | |
| 6,180,683 B1 | 1/2001 | Miller et al. | |
| 6,204,420 B1 | 3/2001 | Miller et al. | |
| 6,313,367 B1 | 11/2001 | Breen | |
| 6,946,524 B2 | 9/2005 | Breuer et al. | |
| 7,097,759 B2 | 8/2006 | Mukkamala | |
| 7,122,112 B2 | 10/2006 | Mukkamala et al. | |
| 7,122,113 B2 | 10/2006 | Cornelisse | |
| 2003/0225076 A1* | 12/2003 | Biwersi | C07C 237/30 514/230.5 |
| 2004/0049008 A1* | 3/2004 | Pedersen | C07D 405/04 506/1 |
| 2010/0107478 A1* | 5/2010 | Zamudio Rivera | C07D 413/06 44/341 |

OTHER PUBLICATIONS https://en.wikipedia.org/w/index.php?title=Dean-Starkapparatus&printable=yes, downloaded on Apr. 27, 2016.*

A. B. Hughes and B. E. Sleebs, Effective methods for the synthesis of N-methyl b-amino acids from all twenty common a-amino acids using 1,3-oxazolidin-5-ones and 1,3-oxazinan-6-ones, Helvetica Chimica Acta—vol. 89 (2006), 2611-2637.* https://en.wikipedia.org/wiki/Paraformaldehyde downloaded on Jul. 17, 2017.*

Hughes, A.B. et al., Effective methods for the synthesis of N-methyl b-mmino acids from all twenty common a-amino acids using 1,3-oxazolidin-5-ones and 1,3-oxazinan-6-ones, Helvetica Chimica Acta, vol. 89 (2006) pp. 2611-2637.

* cited by examiner

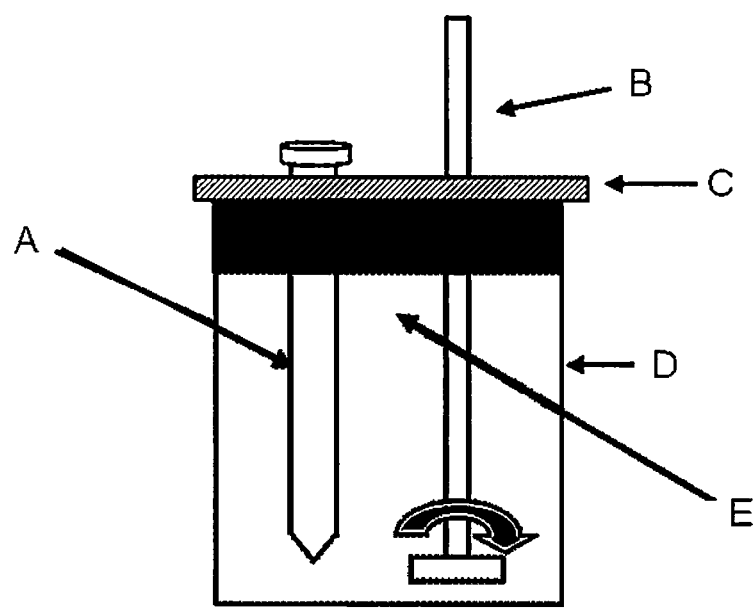

MULTIFUNCTIONAL COMPOSITION BASE 1,3-OXAZINAN-6-ONES WITH CORROSION INHIBITION AND HEAVY ORGANIC COMPOUNDS INHIBITION AND DISPERSANTS AND OBTAINING PROCESS

CROSS-REFERENCE TO RELATED APPLICATIONS

This application is a divisional application of Ser. No. 13/097,236, filed Apr. 29, 2011, which claims the benefit under 35 U.S.C. § 119 of Mexican Patent Application No. MX/a/2010/004777, filed Apr. 30, 2010, which are hereby incorporated by reference in their entirety.

FIELD OF THE INVENTION

This invention relates to the development of new base compounds 1,3-oxazinan-6-ones derivatives of N-alkyl or N-alkenyl or N-cycloalkyl or N-aryl amino propionic acids and paraformaldehyde, and their application and use as multifunctional corrosion inhibitors of ferrous metals used in production processes, transport and storage of crude oil, which are in contact with a high salt content, where the prevailing hydrogen sulfide, and transport and storage of liquid fuels derived from refining oil. In addition, these compounds possess inhibitory and dispersing effects of heavy organic compounds in oil production processes and petroleum refining.

The compounds of this invention and their formulations exhibit low environmental impact.

BACKGROUND OF THE INVENTION

In the oil industry there are various problems that cause daily losses of millions of dollars caused by fall in crude oil production, as well as failures by wear of pipelines and equipment, predominantly from problems of corrosion and deposition of asphaltenes, which is why a global investigations are aimed at generating solutions through a variety of methods to minimize such problems.

Corrosion is a phenomenon that generates millions of dollars in losses in the oil industry because it occurs in virtually all oil production chain from farm to processing.

Corrosion is considered the progressive wear of a metallic material due to its interaction with the surrounding environment.

The particular case of the production and exploration operations for oil, the corrosion phenomenon is directly related to the presence of inorganic salts, hydrogen sulfide, organosulfur compounds, organic acids and carbon dioxide.

The corrosion phenomenon is also commonly found in transportation and storage of products derived from oil refining as gasoline without desulfurize, gasoline with low sulfur, diesel, alkylated gasoline, jet fuel, kerosene, methyl tertiary butyl ether and others.

Usually in the oil industry, the problems of asphaltene deposition and corrosion have been controlled through the use of chemicals, asphaltene inhibitors and dispersants and corrosion inhibitors, which are composed of two main parts known as the head (hydrophilic part) and tail (hydrophobic part).

The particular case of inhibiting and dispersing asphaltenes, the head (hydrophilic part) is a polar group whose function is to interact with the aromatic rings or polar groups of the asphaltenes, while the tail (hydrophobic part) is an aliphatic chain can be linear or branched and which performs the function of forming a stearic barrier that prevents asphaltene molecules interact with each other.

With regard to the phenomenon of corrosion inhibition, corrosion inhibitors widely used in the oil industry are the type of film that is characterized by its molecular structure a head (hydrophilic part) that interacts with the metal surface through two main mechanisms: physisorption, which occurs through an electrostatic attraction and chemisorption manifested through a coordination bond between metal and an atom capable of transmitting electrons, and a tail (hydrophobic part) that can repel water molecules trying to pass into the metal surface.

Because of one of the most economical methods for the prevention and control of these problems is the use of chemical products, the research in this area focuses on the development of chemical compounds that are able to work with more efficient means increasingly aggressive, in addition to complying with environmental regulations that currently govern their use.

Oil is a complex mixture of organic compounds which are broadly classified as: 1) Saturated, 2) Aromatic, 3) Resins and 4) Asphaltenes.

Of these fractions, asphaltenes play an important role because they are one of the fractions that cause more problems as a result of precipitation originating with this, clogging the pores of reservoir rock, clogging pipes, with a consequent fall in crude oil production and therefore the closure of wells, wear on equipment, high costs of maintenance and repair of equipment, among others.

From a chemical structural point, the asphaltene molecular rings are added polyaromatic containing small amounts of heteroatoms (sulfur, nitrogen and oxygen), trace metals (iron, nickel and vanadium), branching linear paraffin and features held together mainly by the type supramolecular interactions $\pi$-$\pi$. These structural features lead to the asphaltenes are more polar fraction in crude oil and tend to precipitate to changes in temperature, pressure and composition are presented in collection, transport or processing of crude oil.

The phenomenon of precipitation of asphaltenes in crude oil occurs when favorable conditions of temperature, pressure and composition, asphaltene particles small, low molecular weight, are associated, grow and generate larger and heavier aggregates that become insoluble in the medium. The high molecular weight and polar nature of these asphaltenes generated that they are disseminated to the bottom of the reservoir, piping or equipment and to adhere firmly to the walls themselves. This phenomenon is known by the name of asphaltene deposition.

It is noteworthy that in the literature does not exist examples of chemical compounds that are capable of inhibiting corrosion and inhibit and dis asphaltenes dispersed through the same molecular structure.

Important examples of corrosion inhibitors used in acid characteristic of the oil industry, we have the following references:

U.S. Pat. No. 3,623,979 discloses obtaining compounds of basic 1-aminoalkyl-2-alkyl imidazolines and their use as corrosion inhibitors for ferrous metals in acidic characteristic of the oil industry. The efficiency of corrosion inhibition of these compounds was evaluated by gravimetric techniques.

U.S. Pat. No. 3,629,104 discloses obtaining organic acid salts of basic compounds derived from 1-aminoalkyl-2-alkyl imidazolines and their use as corrosion inhibitors for ferrous metals in acidic characteristic of the oil industry. The efficiency of corrosion inhibition of these compounds was evaluated by gravimetric techniques.

U.S. Pat. No. 3,390,085 discloses the mixture of imidazoline salt prepared from the reaction of a fatty acid having 6 to 18 carbons with imidazoline selected from the group consisting of 1-aminoalkyl-2-alkyl hydroxyalkyl imidazoline and 1-alkyl-2-imidazolines and their application as corrosion inhibitors in acidic characteristic of the oil industry.

U.S. Pat. No. 4,388,214 discloses corrosion inhibitors synthesized from the reaction of imidazoline or imidazoline salts with sulfur. These compounds are particularly useful for inhibiting corrosion of metal containers caused by carbon dioxide and hydrogen sulfide during transport and storage of crude oil.

U.S. Pat. No. 5,062,992 discloses a corrosion inhibiting formulation for oil and water systems, wherein the formulation is resistant to sludge formation and not to stabilize emulsions water/oil. The corrosion inhibitor includes an imidazoline dissolved in an aromatic solvent, a 2-hidroxy-alkylcarboxylic acid and glycol. The imidazoline is preferably prepared from the reaction of a long chain fatty acid and a polyamine.

Important examples of corrosion inhibitors used in piping, tanks and other combustible liquid handlers references are presented below:

U.S. Pat. No. 4,214,876 (corrosion inhibiting composition) discloses the development of a formulation of the corrosion inhibition for ferrous metals exposed to hydrocarbon fuels made from 75 to 95% of an unsaturated aliphatic carboxylic acid of 16 to 18 carbons and 5 to 25% of a monoalkenyl succinic acid with a chain from 8 to 18 carbons, and to use as a solvent hydrocarbon compounds.

U.S. Pat. No. 4,509,951 (Corrosion Inhibitor for alcohol-based fuels and gasoline-alcohol mixtures) discloses the development of a formulation of the corrosion inhibition for ferrous metals exposed to liquid motor fuels based on alcohol-gasoline blends alcohol consisting of a carboxylic acid poly-unsaturated aliphatic 18-carbon, and the reaction product of a polyamine with a carboxylic acid alkenyl monounsaturated 18-carbon aliphatic or alkenyl succinic anhydride from 8 to 30 carbons.

U.S. Pat. No. 4,511,366 (Liquids fuels and concentrates containing corrosion inhibitors) discloses the development of a formulation of the corrosion inhibition for ferrous metals exposed to liquid alcohol-based fuel or gasoline-alcohol mixtures composed of an aliphatic carboxylic acid poly-unsaturated 16 to 18 carbons and an alkenyl polyamine.

U.S. Pat. No. 4,737,159 (Corrosion inhibitor for liquid fuels) discloses the development of a formulation of the corrosion inhibition for ferrous metals exposed to liquid hydrocarbon fuels made from 35 to 70% by weight of a succinic acid monoalkenyl with a chain ranging from 8 to 18 carbons and 30 to 65% of aliphatic or cycloaliphatic amine containing from 2 to 12 carbons and solvents and aromatic hydrocarbon compounds alcohols of 1 to 4 carbons.

Examples in the literature that mention the development of chemical compounds and their application in crude oil to inhibit or disperse asphaltene deposits can be mentioned the following patents: U.S. Pat. No. 7,122,113, U.S. Pat. No. 7,122,112, U.S. Pat. No. 7,097,759, U.S. Pat. No. 6,946,524, U.S. Pat. No. 6,313,367, U.S. Pat. No. 6,204,420 and U.S. Pat. No. 6,180,683.

U.S. Pat. No. 7,122,113 relates to the use of dendrimeric compounds to solubilize asphaltenes in a mixture of hydrocarbons. Preferably the dendrimeric compound is a hyper-branched polyester amide preferably constructed from succinic anhydride, diisopropanolamine and functionalized with polyisobutenyl succinic anhydride.

U.S. Pat. No. 7,122,112 relates to the development of compounds of structural formula (1):

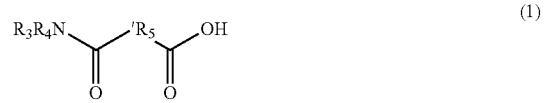

that specifically contain within their structure carboxyl and amide groups, and its application as a dispersant of asphaltenes in crude oil. Within the structural formula (1), $R_5$ is a difunctional alkyl group can vary from $C_1$ to $C_{70}$ and $R_3$ and $R_4$ are independent radicals that can be represented by aryl groups, alkyl, alkyl aryl, heterocyclic or hydrogen. The patent also indicates that these compounds increases demulsibility, reduce viscosity, the formation of sediments, surface fouling and corrosion.

U.S. Pat. No. 7,097,759 relates to the development of compounds of structure formula (2):

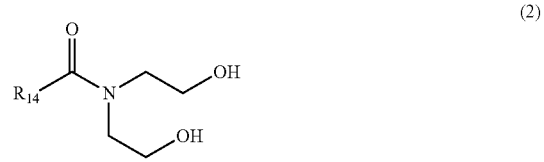

Specifically to contain within its structure a carbonyl group, thiocarbonyl, or imine, and its application as a dispersant of asphaltenes in crude oil. Within the structural formula (2), $R_{14}$ is an alkyl group that may vary from $C_{15}$ to $C_{21}$. The patent also indicates that these compounds increases demulsibility, reduce viscosity, the formation of sediments, surface fouling and corrosion.

U.S. Pat. No. 6,946,524 relates a process for producing polyester-amides by reacting a polyisobutylene with a first agent selected from the group consisting of monounsaturated fatty acid having 3 to 21 carbon atoms and derivatives thereof, and a second agent selected group consisting of monoethanolamine and alkylamines of structural formula (3):

where R represents an alkyl group having from 1 to 4 carbon atoms. The polyester-amides produced are used as stabilizers of asphaltenes in crude oil and crude oil derivatives.

U.S. Pat. No. 6,313,367 discloses that several esters and reaction products of ethers are excellent asphaltene dispersants or inhibitors and may be used in hydrocarbons such as crude oil. Asphaltene inhibitor compounds include 1) esters formed from the reaction of polyhydric alcohols with carboxylic acids, 2) ethers formed from the reaction of glycidyl ethers or epoxides with polyhydric alcohols and 3) esters formed from the reaction of glycidyl ethers or epoxides with carboxylic acids.

U.S. Pat. No. 6,204,420 discloses the development of a new formulation where the asphaltene dispersing action of carboxylic acids can be greatly improved by the addition of relatively small amounts of esters derived from alkylphosphoric acids. The formulation consists of: A) 5 to 99% by weight of a carboxylic acid having more than 4 carbon atoms, an alkyl ethercarboxylic acids with alkyl substituents of $C_{18}$-$C_{22}$, $C_{18}$-$C_{22}$ substituents of alkenyl or $C_6$-C18 substituents of alkylaryl, amidecarboxylic acid or a mixture thereof and B) 1 to 95% by weight of a phosphoric acid mono or diester or mixture thereof, which is substituted by an alkyl group of $C_{18}$-$C_{22}$, $C_{18}$-$C_{22}$ alkenyl, $C_6$ alkylaryl-$C_{18}$ or alkoxylated. Where the sum of A and B is 10% by weight.

U.S. Pat. No. 6,180,683 discloses the development of a new formulation with synergistic effect as asphaltene dispersant. The formulation is composed of 5 to 95% of a compound of structural formulas I or II.

SUMMARY OF THE INVENTION

The present invention overcomes well above the references cited under the new base compounds alkyl, alkenyl or cycloalkyl 1,3-oxazinan-6-ones derivatives of N-alkyl or N-alkenyl or N-cycloalkyl or N-aryl amino propionic acids and paraformaldehyde have the ability to function as corrosion inhibitors for ferrous metals and as inhibitors/dispersants of asphaltenes to be applied in crude oil and products derived from them in order to control fouling and blocked problems that are presented in production processes, transportation, refining and storage of the oil industry.

Therefore, one object of this invention is to provide a composition containing an active base compounds derived from 1,3-oxazinan-6-ones and an aromatic solvent, hydrocarbon, low molecular weight alcohols or a combination thereof. This composition has the multifunctionality of inhibiting corrosion of ferrous metals as well as inhibit and disperse asphaltenes. One aspect of the invention is to provide a method of inhibiting corrosion of ferrous metals and to inhibit deposit of and to disperse asphaltenes in crude oil and hydrocarbon fuels by adding an effective amount of the 1,3-oxazinan-6-ones of the invention.

Another object of this invention is to provide an active compound such as alkyl, alkenyl or cycloalkyl 1,3-oxazinan-6-ones and their use as corrosion inhibitors with inhibitory and dispersing asphaltenes in petroleum. The compounds of the invention are suitable as corrosion inhibitors and for inhibiting deposit of asphaltenes, and dispersing asphaltenes in crude oil and hydrocarbon fuels.

Another object of the present invention is to provide a process for obtaining the active compound alkyl, alkenyl or cycloalkyl 1,3-oxazinan-6-ones. The 1,3-oxazinan-6-ones are prepared by reacting an N-alkyl, N-alkenyl, N-cycloalkyl or N-aryl propionic acid and paraformaldehyde.

BRIEF DESCRIPTION OF THE DRAWINGS

It provides the following FIG. 1, in order to clearly understand the test of inhibition of corrosion of base compounds 1,3-oxazine-6-ones and their application as multifunctional corrosion inhibitors and inhibitor/dispersants of heavy organic compounds, and serving as a reference in the example application.

FIG. 1 shows the inhibition test device consisting of a test specimen (A), a digitally controlled stirrer (B), a cover of poly (tetrafluoroethylene) (C), a glass (D) hydrocarbon-water mixture (E).

DESCRIPTION OF THE INVENTION

New compounds were developed base 1,3-oxazinan-6-ones derivatives of N-alkyl or N-alkenyl or N-cycloalkyl or N-aryl amino propionic acids and paraformaldehyde, and their application as multifunctional corrosion inhibitor with inhibitory and dispersant asphaltenes properties in production processes, transportation and oil refining, and transport and storage of hydrocarbons, with the following structural formula (4):

In the structural Formula (4), R is a linear or branched alkyl chain of 6 to 18 carbons or a linear or branched chain alkenyl of 8 to 20 carbons or aromatic cycloalkyl of 5 to 12 carbons, $R_1$ is a radical that can be represented by the groups—H, or —$CH_3$ and $R_2$ is a radical that can be H or $CH_3$.

The compounds of this invention were prepared according to the following scheme (5).

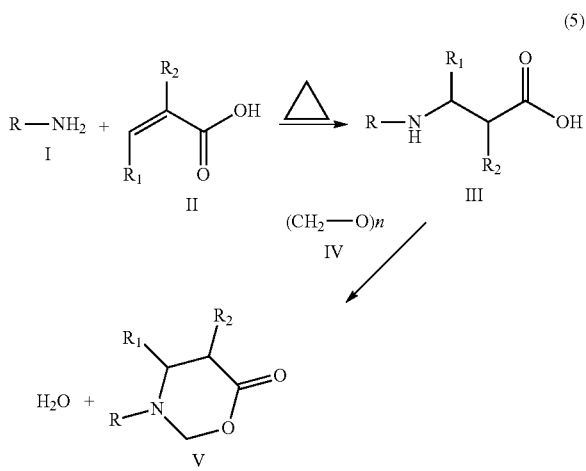

In the above reaction scheme, Reaction Product V corresponds to the compound of Formula (4). In the reaction scheme, R, $R_1$ and $R_2$ are as defined above.

The first stage of the obtaining process is the reaction between an alkyl or alkenyl or cycloalkyl or aromatic amine of Formula I with an alpha-beta unsaturated carboxylic acid of formula II to obtain the corresponding N-alkyl or N-alkenyl or N-cycloalkyl or N-aryl propionic acid of structural formula III. The molar ratio of amine alkyl or alkenyl or aromatic carboxylic acid with respect to alpha-beta unsaturated may vary in the range of 1:5 to 5:1, preferably in the range of 1:1 to 2:1 and the reaction is carried out in the absence of solvents. The reaction time and temperature depends on the structure of the alkyl or alkenyl or cycloalkyl or aromatic amine and alpha-beta unsaturated carboxylic acid, and the temperature at which the reaction is carried out. Usually the reaction time varies in the range of 1 to 24 hours and the reaction temperature varies in the range of 80 to 200° C.

For alkyl amines can be selected from the following examples: hexylamine, heptylamine, octylamine, nonylamine, decylamine, undecylamine, dodecylamine, tridecylamine, tetradecylamine, pentadecylamine, hexadecylamine, heptadecylamine, octadecylamine or a linear or branched alkenyl amine selected examples: oleylamine, linoleylamine, eurocylamine, behenylamine and taloylamine, or a cycloalkyl or aromatic amine derivative of the examples: cyclohexylamine, benzylamine, aniline, among others.

With respect to acid alpha-beta unsaturated carboxylic preferred for this invention are: acrylic acid, methacrylic acid, crotonic acid and isocrotonic acid.

The second stage of the production process consists of reacting the corresponding N-alkyl or N-alkenyl or N-cycloalkyl or N-aryl propionic acids with paraformaldehyde in the structural formula IV to obtain the corresponding 1,3-oxazinan-6-ones derived of structural formula V. The molar ratio of N-alkyl or N-alkenyl or N-cycloalkyl or N-aryl amino propionic and paraformaldehyde can vary in the range of 1:0.5 to 1:4 preferably in the range of 1:1 to 1:2 and reaction can be carried out in bulk or in the presence of an inert hydrocarbon solvent among which are preferably toluene, xylene mixtures, o-xylene, m-xylene, p-xylene, kerosene and jet fuel. The reaction time depends on the structure of N-alkyl or N-alkenyl or N-cycloalkyl or N-aryl propionic acids, as well as temperature and pressure at which the reaction is carried out. Usually the reaction time varies in the range of 1 to 24 hours, the reaction temperature varies in the range of 60 to 200° C., preferably in the range of 90 to 180° C. and pressure which holds the reaction varies in the range of 60 to 760 mmHg, preferably in the range of 400 to 585 mm Hg. Paraformaldehyde is a condensation reaction product of formaldehyde having the formula

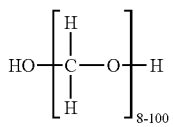

having a typical degree of polymerization of 8-100.

The compounds of the present invention and their formulations are useful as: Additives are added in crude oil and fuel oil as fuel without desulfurizing, fuel with low sulfur, diesel, methyl tertbutyl ether, alkylated gasoline, kerosene and jet fuel, to prevent and control corrosion in wells, pipelines and tanks storage. The additive concentration needed to control corrosion of ferrous metals depends on the type of oil or fuel oil derivative thereof, and the presence of other additives.

Additives are added in crude oil and products derived from them to prevent and control the deposition of asphaltenes in wells, pipelines and refining plants. The additive concentration needed to control the deposition of asphaltenes depends on the type of crude oil or derivative thereof, and the presence of other fuel additives.

In general, the concentration of the compounds of this invention varies in crude oil in the range 1 to 2000 parts per million (ppm), preferably from 1 to 1000 ppm.

When another class of additives that control the deposition of organic compounds is present, a smaller amount of additive may be used, and in the case of fuel varies in the range of 1 to 50 parts per million (ppm), preferably from 1 to 20 ppm.

The 1,3-oxazine-6-ones of the present invention can be formulated as a concentrate using inert organic solvent having a boiling point between 75 and 300° C., preferably hydrocarbon solvents such as benzene, toluene, mixed xylenes, o-xylene, m-xylene and p-xylene, diesel, kerosene, jet fuel, alcohols, aliphatic branched and unbranched containing in its structure from 3 to 10 carbon atoms, such as isopropanol, butanol and pentanol, and mixtures of hydrocarbon solvents with aliphatic branched and unbranched. The amount of active compound of Formula 4 in the formulation ranges from 10 to 90 wt %, preferably from 25 to 75 wt %.

The 1,3-oxazine-6-ones of the present invention can be dosed from 5 to 2000 ppm, depending on conditions of operation of the well or the pipe containing the crude oil or liquid fuel.

EXAMPLES

Here are some practical examples for better understanding of the present invention, without limiting its scope.

Example 1

Process for obtaining 3-(octadec-9-enyl)-1,3-oxazine-6-one (Product 1). In a flask ball three-necked 500 ml equipped with a magnetic stirrer, a dropping funnel, a thermometer and a condenser were added 50 g (0.187 mol) of oleylamine at a temperature of 40° C. with vigorous stirring was slowly added to 13.48 g (0.187 mol) acrylic acid. The reaction is exothermic and the temperature under these conditions rises gradually to 90° C. The reaction mixture was stirred under these conditions for 2 hours and then increased to 100° C., thus obtaining a very viscous pale yellow, then to a temperature of 30° C. were added 2.8 g (0.094 mol) of paraformaldehyde, and temperature was increased to 93° C. at a pressure of 465 mmHg to remove water of reaction and finally obtained 65 g of Product 1, the spectroscopic features are:

FTIR (cm$^{-1}$): 3004.9, 2921.6, 2852.1, 1656.1, 1463.5, 1376.9, 1305.4, 1106.1, 956.9, 721.2. $^1$H NMR (CDCl$_3$), 200 MHz, δ (ppm): 5.28, 3.91, 3.24, 2.84, 2.36, 1.94, 1.21, 0.82. $^{13}$C NMR (CDCl$_3$), 50 MHz, δ (ppm): 167.3, 129.7, 129.6, 68.4, 52.4, 48.1, 44.7, 32.5, 31.8, 29.4, 29.2, 27.0, 22.5 y 13.9.

Example 2

Process for obtaining the 3-octadecyl-1,3-oxazine-6-one (Product 2). In a flask ball three-necked 500 ml equipped with a magnetic stirrer, a dropping funnel, a thermometer and a condenser were added 50 g of octadecylamine and at a temperature of 40° C. with vigorous stirring was slowly added to 13.4 g of acrylic acid. The reaction is exothermic and the temperature under these conditions rises gradually to 90° C. The reaction mixture was stirred under these conditions for 2 hours and then increased to 100° C., thus obtaining a very viscous pale yellow, then at a temperature of 30° C. were added 2.8 g of paraformaldehyde, and increase temperature at 93° C. at a pressure of 465 mmHg to remove water of reaction and finally obtained 64 g of Product 2, the spectroscopic features are:

FTIR (cm$^{-1}$): 2922.1, 2852.1, 1655.3, 1461.5, 1375.8, 1302.6, 1105.7, 956.5, 721.3. $^1$H NMR (CDCl$_3$), 200 MHz, δ (ppm): 3.93, 3.25, 2.86, 2.38, 1.20, 0.83. $^{13}$C NMR (CDCl$_3$), 50 MHz, δ (ppm): 167.4, 68.4, 52.5, 48.2, 44.8, 31.8, 29.6, 29.5, 22.6, 22.5 y 14.0.

Example 3

Process for obtaining the 3-tetradecyl-1,3-oxazine-6-one (Product 3). In a flask ball three-necked 500 ml equipped with a magnetic stirrer, a dropping funnel, a thermometer and a condenser were added 50 g of tetradecylamine and at a temperature of 40° C. with vigorous stirring was slowly added to 16.7 g of acrylic acid. The reaction is exothermic and the temperature under these conditions rises gradually to 90° C. The reaction mixture was stirred under these conditions for 2 hours and then increased to 100° C., thus obtaining a very viscous pale yellow, then to a temperature of 30° C. were added 3.5 g of paraformaldehyde, and increase temperature at 93° C. at a pressure of 465 mmHg to remove water of reaction and finally obtained 69 g of Product 3, the spectroscopic features are:

FTIR (cm$^{-1}$): 2921.4, 2853.4, 1657.1, 1462.3, 1375.3, 1304.5, 1108.2, 955.8, 722.4. $^1$H NMR (CDCl$_3$), 200 MHz, δ (ppm): 3.95, 3.21, 2.85, 2.33, 1.23, 0.86. $^{13}$C NMR (CDCl$_3$), 50 MHz, δ (ppm): 167.1, 68.6, 52.7, 48.1, 44.6, 31.9, 29.7, 29.6, 22.7, 22.5 y 14.0.

Example 4

Process for obtaining the 3-dodecyl-1,3-oxazine-6-one (Product 4). In a flask ball three-necked 500 ml equipped with a magnetic stirrer, a dropping funnel, a thermometer and a condenser were added 50 g (0.187 mol) of dodecylamine and a temperature of 40° C. with vigorous stirring was slowly added to 19.4 g of acrylic acid. The reaction is exothermic and the temperature under these conditions rises gradually to 90° C. The reaction mixture was stirred under these conditions for 2 hours and then increased to 100° C., thus obtaining a very viscous pale yellow, then to a temperature of 30° C. were added 4.1 g of paraformaldehyde, and increase temperature at 93° C. at a pressure of 465 mmHg to remove water of reaction and finally obtained 72 g of Product 4, the spectroscopic features are:

FTIR (cm$^{-1}$): 2921.6, 2852.4, 1654.1, 1461.9, 1373.4, 1303.6, 1109.5, 951.5, 723.2. $^1$H NMR (CDCl$_3$), 200 MHz, δ (ppm): 3.97, 3.26, 2.83, 2.37, 1.15, 0.79. $^{13}$C NMR (CDCl$_3$), 50 MHz, δ (ppm): 167.2, 68.4, 52.2, 48.2, 44.4, 31.7, 29.5, 29.4, 22.5 y 13.9.

Performance Testing

To evaluate the efficiency of corrosion inhibition in an environment characteristic of pipes and tanks that transport and store crude oil, used the gravimetric technique known as dynamic testing of wheel and electrochemical technique known as linear polarization. The following describes each test procedures and results.

Determination of the Corrosion Inhibition Efficiency Through NACE 1D-182 Method

Gravimetric test is commonly called dynamic wheel (Wheel test) that simulates the corrosive environment characteristic of oil production, is a dynamic procedure developed for fluids (oil, water and inhibitor).

For this test using a specimen of 1010 carbon steel with dimensions 2,540×1,270 cm×0.025 cm, which is weighed and placed inside a bottle containing 180 ml of an emulsion or brine aggressive environments simulating acids characteristic of the oil industry, and a certain amount of corrosion inhibitor can vary from 0 to 500 ppm. The bottle is sealed and placed in a hole of a wheel of 58.4 cm in diameter that is within a range, then the oven temperature is increased to 70° C., while the wheel rotates at 30 rpm for about 46 hours. At the end of the test, specimen is removed from the bottle, washed consecutively with chloroform, acetone, water, a solution of diluted hydrochloric acid, a potassium bicarbonate solution with 5 in weight and water, clean with wire brushing, rinse with soap and water, dried in an oven at 60° C. and reweighed. Depending on weight loss and with reference to a target is calculated efficiency of corrosion inhibition, while for the evaluation of the corrosion rate reported in thousandths of an inch per year (mpy) are taken into account the following parameters the specimen: a) weight loss, b) area, c) density d) test time.

Gravimetric test is commonly called dynamic wheel (Wheel test) that simulates the corrosive environment characteristic of oil production, is a dynamic procedure developed for fluids (oil, water and inhibitor).

Testing Equipment and Reagents a) Evaluating dynamic for corrosion inhibitors with temperature controller, stirrer speed of 30 rpm and capacity for 52 bottles of 180 ml.

b) Bottles of 200 ml capacity.

c) Coupon SAE 1010 carbon steel, dimension 2,540×1, 270×0.025 cm (1"×0.5"×0.010").

d) Glassware for the preparation of a corrosive environment. This consists of a glass reactor of 2 liter, equipped with a cooling bath, mechanical stirrer, bubbler for gas (nitrogen and hydrogen sulfide), has an outlet connected to two traps in series (the first with sodium hydroxide in pellet form and the second with another sodium hydroxide solution 20% in weight), so that hydrogen sulfide does not contaminate the environment.

e) Potentiometer for measuring pH.

The test conditions are shown in Table 1, while the composition of the brine used is shown in Table 2.

TABLE 1

| Test Conditions, NACE 1D-182 method | |
|---|---|
| Temperature | 70° C. |
| Aqueous medium | Synthetic brine with 600 ± 50 ppm de H$_2$S |
| Test time | 46 hours |
| Organic medium | Kerosene |
| Volume ratio Synthetic brine/organic medium | 90/10 |
| Test volume | 180 ml |
| pH | 4 |
| Metals coupons | Steel SAE 1010 |

TABLE 2

| Brine composition used, 1D-182 NACE method. | |
|---|---|
| Salts | Amount (g/l) |
| NaCl | 60.0 |
| CaCl$_2$•H$_2$O | 6.0 |
| MgCl$_2$•6H$_2$O | 10.48 |
| Na$_2$SO$_4$ | 3.5 |

Results

The difference in weight of the coupons before and after being exposed to corrosive liquid for 46 hours, is a direct indication of metal lost due to corrosion.

The efficiency of corrosion inhibition is obtained by comparing the reference coupon wear with the wear of the coupons with corrosion inhibitor at different concentrations, using the following formula:

$\%E = (Vo - V/V) \times 100$

Where:
Vo=Corrosion velocity of reference coupon
V=Corrosion velocity of coupon with corrosion inhibitor
Table 3 shows the results of the Products 1 to 6 at different concentrations.

TABLE 3

| Example | Concentration (ppm) | Corrosion velocity, (mpy's)* | Efficiency, (%) |
|---|---|---|---|
| Reference | 0 | 41.6 | 0 |
| Product 1 | 10 | 2.2 | 94.9 |
|  | 25 | 3.5 | 91.9 |
|  | 50 | 2.4 | 94.5 |
|  | 75 | 2.0 | 95.2 |
| Product 2 | 10 | 5.8 | 86.4 |
|  | 25 | 4.2 | 90.1 |
|  | 50 | 2.8 | 91.4 |
|  | 75 | 0.6 | 98.5 |
| Product 3 | 10 | 4.6 | 89.3 |
|  | 25 | 1.4 | 96.7 |
|  | 50 | 1.4 | 96.7 |
|  | 75 | 1.6 | 95.9 |
| Product 4 | 10 | 32.4 | 24.3 |
|  | 25 | 26.4 | 38.2 |
|  | 50 | 5.2 | 87.9 |
|  | 75 | 2.9 | 93.0 |

*mpy's: thousandths of an inch per year

Determination of the Efficiency of Corrosion Inhibition by the Method NACE™-0172

Test Description

Test Method NACE™-0172 is to determine the corrosive properties of gasoline, jet fuel and distillate fuels that found in pipelines and storage tanks. Also includes information on metal specimen preparations, equipment and a system for ranking the test samples with corrosion inhibitor.

Testing Equipment and Apparatus

The apparatus consists of:
A temperature measuring device, and
One bathroom. Should be used a thermally controlled bath of mineral oil capable of maintaining a temperature in the test sample 38±1° C. The bathroom must have a cover with holes to accommodate the test glass and the temperature measuring device.

The test device used by the NACE™-0172 method to determine the efficiency of corrosion inhibition posed by gemini surfactants of the present invention, illustrated by FIG. 1, consists of a test specimen (A), a digitally controlled stirrer (B), a cover of poly (tetrafluoroethylene) (C), a glass (D), and hydrocarbon-water mixture (E).

The sample must be a steel yarn 81.0×12.7 mm, the steel shall conform to UNS*G10150 (Grade 1015), UNS G10180 (1018), UNS G10200 (1020) or UNS G10250 (1025) ASTM A108, used with a plastic handle of poly(tetrafluoroethylene) (PTFE). (*Unified Numbering System).

Test Procedure

Add 300 ml of fuel to the test vessel and dispensed corrosion inhibitor to the desired concentration, the glass is placed in an oil bath at a temperature of 38±1° C. after 30 minutes of continuous stirring add 30 ml of distilled water, and agitation continued for three hours. Subsequently the sample is removed, and left to drain and washed with toluene or xylene followed by acetone.

Sample Qualification

The rating should be based solely on the portion of the sample that remained in the test fluid. The corrosion products formed during the test have had limited opportunity to darken, and all deposits of solids not removed by washing of toluene and acetone should be considered as products of corrosion. Marks on the circle can occur during polishing and should not be interpreted as corrosion, classification is based according to Table 4.

TABLE 4

Samples qualification NACE TM-0172 method.

| Qualification | Percentage of corroded surface |
|---|---|
| A | 0 |
| B++ | Less than 0.1 |
|  | (2 or 3 spots of no more than 1 mm in diameter). |
| B+ | Less than 5 |
| B | 5-25 |
| C | 25-50 |
| D | 50-75 |
| E | 75-100 |

Table 5 shows the results of Product 1 with a variety of liquid fuels.

Table 6 shows the results of the Products 2 to 6 on gasoline with low sulfur content at different concentrations.

TABLE 5

| Product | Concentration, (ppm) | Test medium, (fuel) | Qualification, (NACE TM-0172) |
|---|---|---|---|
| Reference | 0 | All fuels | E |
| 1 | 10 | Primary gasoline (without desulfurization) | B++ |
|  | 10 | Magna gasoline | A |
|  | 10 | Premium gasoline | A |
|  | 10 | Diesel | B++ |
|  | 10 | MTBE | A |
|  | 10 | Alkylated gasoline | A |
|  | 10 | Magna gasoline/ Ethanol (50:50) | A |

TABLE 6

| Product | Concentration, (ppm) | Qualification, (NACE TM-0172) |
|---|---|---|
| Reference | 0 | E |
| 2 | 10 | B++ |
|  | 25 | A |
| 3 | 10 | B+ |
|  | 25 | A |
| 4 | 10 | B+ |
|  | 25 | B++ |

Determination of the Efficiency of Corrosion Inhibition by Electrochemical Techniques

Equipment Used

It used a glass electrochemical cell, reference electrode, working electrode, counter electrode, ph meter, multimeter, potentiostat/galvanostat Autolab PGSTAT 30 71410. Was also held for the preparation of the bitter brine of pH 4, and the dissolution of chemicals in isopropanol in order to prepare a solution of 1,000 ppm in 100 mL.

Test Procedure

A specimen of carbon steel 1010 with area of 0.5 cm$^2$ is grinding with #600 sandpaper. The bitter brine is the same as was used for the gravimetric technique. Polarization curves were generated linear open-circuit potential ±25 mV. When the test is obtained polarization curve, which is analyzed to determine the corresponding corrosion rate. To make a new experiment is necessary to perform the roughing electrode is placed in the cell and generate another curve. This procedure is repeated until there is a coincidence of at least two curves. The experiments were performed at room temperature with magnetic stirring and bitter brine adjusted to pH 4.0±1. The corrosion rate (mpy) is determined through manipulation of the curve using the program of the potentiostat.

Table 7 shows the results for Products 1 to 4 at different concentrations:

TABLE 7

| Product | Concentration, (ppm) | Corrosion velocity, (mpy's) | Efficiency, (%) |
|---|---|---|---|
| Reference | 0 | 72 | 0 |
| 1 | 25 | 18 | 75 |
|  | 50 | 12 | 83 |
| 2 | 25 | 21 | 71 |
|  | 50 | 18 | 73 |

Performance evaluation as inhibitors of precipitation or deposition of asphaltenes and asphaltene aggregates as dispersing the compounds of the present invention is carried out through two different tests:

I) Test measuring the mass deposited on metal surface through an electrostatic field and, II) Measurement test asphaltenes dispersed in heptane-crude oil through UV-Visible spectroscopy. Measuring the dispersion of asphaltenes in crude oil-heptane mixtures.

I) Test Measuring the Mass Deposited on Metal Surface Through an Electrostatic Field This test consists of inducing the deposition of organic material on a metallic surface by means of applying an electrostatic field. The asphaltenic aggregates suspended in crude oil, in spite of not possessing a net electrical charge, due to their electronic density, are sensitive to electrostatic fields having certain intensity, which generates an electrostatic charge in them that induces their deposition on the plate connected to the positive pole of the potentiometer. A Teflon array, having two parallel metallic stainless steel plates separated by 5 mm, is introduced to each cell; the system is balanced at the test temperature, and the electric field is applied during 24 h, by the end of which, the plates (previously weighted) are removed from the cells and left to drain for 8 h, to afterwards be weighted and the quantity of deposited material to be determined. The efficiency of the compound is determined relative to the difference between the mass deposited on the plate from the sample without inhibitor, the reference, and the mass deposited from a crude sample with inhibitor.

$$\text{Efficiency} = \frac{\text{Reference mass deposition} - \text{Inhibitor mass deposition}}{\text{Reference mass deposition}}$$

Test conditions:
Temperature: 50° C.
Pressure: 0.0774 MPa (ambient)
Crude petroleum sample volume: 500 cm$^3$
Voltage: 800 V
Amperage: 3000 mA
Inhibitor dosage: 1000 ppm (mg/L)
Oil (sample A)

Below are shown in Table 8, the characteristics of the oil (Sample A) used in the tests I and II.

TABLE 8

Characteristics of the oil (Sample A) used in performance tests I and II.

| Properties | A |
|---|---|
| Density to 25° C. and 585 mm Hg | 0.852 |
| Composition (% w) |  |
| Crystallizable paraffins | 6.13 |
| Saturated hydrocarbon fraction | 54.80 |
| Aromatic hydrocarbon fraction | 23.57 |
| Polar hydrocarbon fraction (resins) | 21.21 |
| Asphaltenes | 0.41 |

The test results are shown in Table 9

TABLE 9

Test results

| Product | Mass deposited (mg) | Efficiency, (%) |
|---|---|---|
| Oil crude | 758.2 | 0 |
| 1 | 10.3 | 98.6 |
| Commercial 1 (Polyalkenyl succinimides) | 68.2 | 95.0 |

II) Measurement Test Asphaltenes Dispersed in Heptane-Crude Oil Through UV-Visible Spectroscopy. Measuring the Dispersion of Asphaltenes in Crude Oil-Heptane Mixtures The test is based in the fact that asphaltenes are soluble in aromatic hydrocarbons, but insoluble in aliphatic hydrocarbons such as n-heptane. The dispersing capacity of a compound can be evaluated dissolving a small amount of crude oil in aromatic solvent and then adding the aliphatic hydrocarbon to provoke asphaltene precipitation. Given that asphaltenes absorb energy at UV-Visible region of electromagnetic spectrum, it is possible to have a proportional estimation of the amount of precipitated asphaltene by measuring the absorbance of an aliquot of the resulting supernatant liquid at a suitable wavelength within the UV-Visible region. Variants of this methodology have been used to determine the remnant concentration of asphaltene in solution, as a measure of the dispersing efficiency of chemical additives. Among the more representative documents are U.S. Pat. No. 6,313,367 and U.S. Patent Publication No. 2004/0039125.

During the development of the present invention it was determine that the optimum wavelength to quantify the asphaltene dispersion is 510 nm.

The procedure that has been design for this test consists of:

Preparing a concentrate solution of 10,000 ppm of additive in toluene. Then 9.5 ml of n-heptane and 0.5 ml of concentrated additive to reach additive concentration of 100, 250, 1000 and 500 (mg/L) were added to a test tube, and then the mixture was vigorously agitated for 30 seconds and leave in repose for 24 hours. Afterwards a heptane reference was prepare, 9.5 ml of n-heptane and 0.5 ml of toluene were added to a test tube, immediately afterwards 0.1 ml of light crude oil or 0.1 ml of a 15% solution of heavy crude oil in toluene were also added, then the test tube was vigorously agitated for 30 seconds and leave in repose for 24 hours.

After rest time, take 3 mL of the supernatant of the dispersion, taking care not to disturb the sediment, filter through a 0.45 mm syringe and transfer to the cell of UV-Visible spectrophotometer.

Measuring the maximum absorbance wavelength of 510 nm selected. Calculate the scattering efficiency using the following equation to establish the efficiency percentage of dispersant:

$$\% \text{ Efficiency} = \frac{\text{Test tube absorbance} - \text{Reference absorbance}}{\text{Reference absorbance}} \times 100$$

The test results are shown in Table 10.

TABLE 10

Test Results of dispersant efficiency determination through UV-Visible spectroscopy, samples of crude oil A.

| Product | Dosage (ppm) | Absorbance (U.A.) | Efficiency, (%) |
|---|---|---|---|
| White | — | 0.4025 | — |
| 1 | 100 | 0.7745 | 92 |
|  | 250 | 0.7824 | 94 |
|  | 500 | 0.7964 | 98 |
| 2 | 500 | 0.6528 | 62 |
| Commercial 1 (Polyalkenyl succinimides) | 500 | 0.7256 | 91 |

Table 10 shows the comparison between the efficiencies for Product 1 and the commercial Product 1 (derived from polyalkenyl succinimide), it is important to mention that the Product 1, the object of this invention, and present a good efficiency (98.6%). On the electrodeposition test and 98% in testing the dispersion of organic compounds by UV oil has the technical advantage of running as well as a corrosion inhibitor, which was confirmed in the evaluation tests-1D-182 NACE, NACE™-0172 and linearly polarized electrochemical technique earlier in the present invention.

What is claimed is:

1. A process for obtaining 1,3-oxazinan-6-one by the following synthesis route:

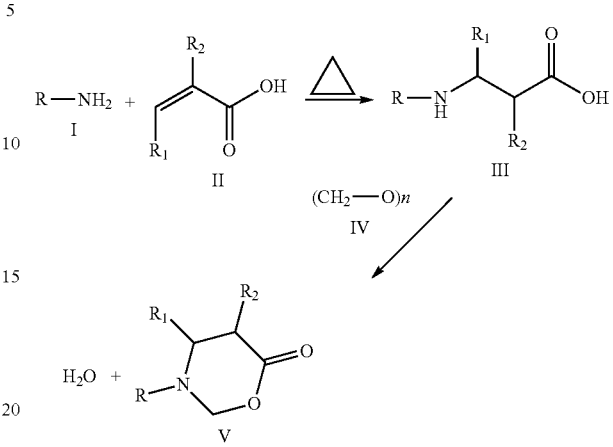

and including two stages of reaction:
I) a first stage of reacting an alkyl or alkenyl or cycloalkyl or aromatic amine of Formula I with an alpha-beta unsaturated carboxylic acid of formula II in the absence of a solvent to obtain the corresponding N-alkyl or N-alkenyl car N-cycloalkyl or N-aryl propionic acid of structural formula III, and
II) a second stage of reacting said corresponding N-alkyl or N-alkenyl or N-cycloalkyl or N-aryl propionic acids of structural formula III with paraformaldehyde of structural formula IV in the absence of a solvent or in the presence of an inert hydrocarbon selected from the group consisting of toluene, xylene, kerosene, and jet fuel to obtain the corresponding 1,3-oxazinan-6-ones of structural formula V, wherein R is a linear or branched alkyl chain of 6 to 18 carbons, a linear or branched chain alkenyl of 8 to 20 carbons or aromatic cycloalkyl having 5 to 12 carbons, $R_1$ is a radical selected from the group consisting of H and —$CH_3$, and $R_2$ is a radical selected from the group consisting of H and $CH_3$.

2. The synthesis process of claim 1, wherein a molar ratio of said alkyl or alkenyl or cycloalkyl or aromatic amine of Formula I with respect to said alpha-beta unsaturated carboxylic acid of Formula II is in the range of 1:5 to 5:1 in the absence of solvents.

3. The synthesis process of claim 1, wherein a reaction time in said first stage is in the range of 1 to 24 hours.

4. The synthesis process of claim 1, wherein a reaction temperature of said first stage is in the range of 80 to 200° C.

5. The synthesis process of claim 1, wherein said alkyl or alkenyl or cycloalkyl or aromatic amine of Formula I is selected from the group consisting of hexylamine, heptylamine, octylamine, nonylamine, decylamine, undecylamine, dodecylamine, tridecylamine, tetradecylamine, pentadecylamine, hexadecylamine, heptadecylamine, octadecylamine, oleylamine, linoleylamine, eurocylamine, behenylamine, taloylamine, cyclohexylamine, aniline, and benzylamine.

6. The synthesis process of claim 1, wherein said alpha-beta unsaturated carboxylic acid of formula II is selected from the group consisting of acrylic acid, methacrylic acid, crotonic acid and isocrotonic acid.

7. The synthesis process of claim 1, wherein a molar ratio of said N-alkyl, N-alkenyl, N-cycloalkyl or N-aryl propionic acid and said paraformaldehyde is 1:0.5 to 1:4.

8. The synthesis process of claim 1, wherein a reaction temperature of said second stage is in the range of 60 to 200° C. and a pressure in said second stage is in the range of 60 to 760 mmHg.

9. The synthesis process of claim 1, wherein a molar ratio of said N-alkyl, N-alkenyl, N-cycloalkyl or N-aryl propionic acid and said paraformaldehyde is 1:1 to 1:2, a reaction temperature of said second stage is 90-180° C. and a reaction pressure in the second stage is 400 to 555 mmHg.

10. A process for obtaining 1,3-oxazinan-6-one by the following synthesis route:

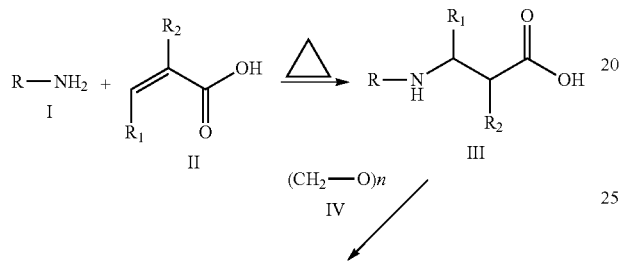

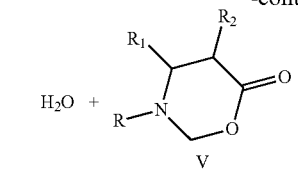

and including two stages of reaction:
  I) a first stage consisting of reacting an alkenyl amine of Formula I with an alpha-beta unsaturated carboxylic acid of formula II to obtain the corresponding N-alkenyl propionic acid of structural formula III in the absence of a solvent, and
  II) a second stage consisting of adding paraformaldehyde of structural formula IV to said N-alkenyl propionic acid of structural formula III, and reacting said corresponding N alkenyl propionic acids of structural formula III with said paraformaldehyde of structural formula IV to obtain said corresponding 1,3-oxazinan-6-ones of structural formula V,
wherein R is a linear alkyl chain having 18 carbons, $R_1$ is H, and $R_2$ is H.

11. The process of claim 1, wherein the molar ratio of the said alkyl, alkenyl, cycloalkyl or aromatic amine of Formula I with respect to said alpha-beta unsaturated carboxylic acid of Formula II is in the range of 1:1 to 2:1.

* * * * *